(12) United States Patent
Guerrero

(10) Patent No.: US 6,508,791 B1
(45) Date of Patent: Jan. 21, 2003

(54) INFUSION DEVICE CARTRIDGE

(76) Inventor: Ramon Guerrero, 5001 Hudson Dr., Plano, TX (US) 75093

( * ) Notice: Subject to any disclaimer, the term of this patent is extended or adjusted under 35 U.S.C. 154(b) by 0 days.

(21) Appl. No.: 09/493,558

(22) Filed: Jan. 28, 2000

(51) Int. Cl.⁷ .............................................. A61M 5/178
(52) U.S. Cl. ......................... 604/183; 604/191; 604/247
(58) Field of Search ............................. 604/892.1, 6.12, 604/27, 36, 506, 512, 124, 125, 68, 71, 72, 82, 151, 173, 258, 183, 184, 186, 491, 187, 191, 247

(56) References Cited

U.S. PATENT DOCUMENTS 4,795,441 A * 1/1989 Bhatt ......................... 604/124
5,411,490 A * 5/1995 Tennican et al. ............ 604/236
6,102,897 A * 8/2000 Lang .......................... 604/246

* cited by examiner

Primary Examiner—Anhtuan T. Nguyen
Assistant Examiner—Matthew F. DeSanto
(74) Attorney, Agent, or Firm—R. Darryl Burke; McKool Smith, P.C.

(57) ABSTRACT

An infusion apparatus comprises a plurality of ports, a plurality of one-way directional valves, and a joint. Each port is adapted to receive and secure a syringe to allow for a flow of a liquid through the syringe into the port. Each one-way directional valve is in fluid communication with a respective port of the plurality of ports to enable the liquid to flow away from the port. The joint has a plurality of inputs to receive the flow from the plurality of one-way directional valves. The inputs are in fluid communication with each individual port of the plurality of ports. The joint has an output.

27 Claims, 7 Drawing Sheets

INFUSION DEVICE CARTRIDGE

PARTIAL WAIVER OF COPYRIGHT PURSUANT TO 1077 O.G. 22(Mar. 20, 1987)

©Copyright. 2000. Dr. Ramon Guerrero. All of the material in this patent application is subject to copyright protection under the copyright laws of the United States and of other countries. As of the first effective filing date of the present application, this material is protected as unpublished material.

However, permission to copy this material is hereby granted to the extent that the owner of the copyright rights has no objection to the facsimile reproduction by any one of the patent document or patent disclosure, as it appears in the United States Patent and Trademark Office patent file or records, but otherwise reserves all copyright rights whatsoever.

FIELD OF INVENTION

The present invention generally relates to the medical devices, particularly anesthesiology, critical care and anesthesia devices used to administer anesthesia medications to patients, prior to surgery and during surgery.

BACKGROUND

The intravenous administration of medicines by medical personnel, such as anesthetic agents by anesthesiologist, is a complex procedure. Unfortunately, this procedure is further complicated by current instrumentation and medical devices used to administer these medicines, particularly everyday syringes with the ever-dangerous needle. For example, as a point of review, multiple anesthesia medications are currently administered closely after one another, which requires the careful and rapid use of multiple syringes containing different drugs, namely (i) a hypnotic agent; (ii) a muscle relaxant; and (iii) a narcotic. These multiple syringes are typically used to transfer the medication into an intravenous port, one at a time, preferably in rapid succession to minimize the patient's pain and, in some cases, to expedite the patient's drowsiness or unconsciousness. Consequently, an anesthesiologist typically must rapidly perform the following steps: (i) take one syringe; (ii) insert it into an intravenous catheter; (iii) press down on the syringe to transfer the medicine into the intravenous catheter into the patient; (iv) remove the syringe; (v) place it somewhere in the patient's hospital room, such as on the patient's bed; (vi) take a second syringe and repeat the steps; and, then, (vii) take a third syringe and repeat steps (i) through (v). Some doctors actually use duct tape to tape the syringe and intravenous catheter together and/or to tape the syringe to the patient's bed.

The current approach described above has a number of drawbacks. For instance, it does not easily allow the dosage to be easily controlled, as needed, from patient to patient, because of the difficulties in reinserting the syringe into the intravenous catheter, as the syringe may become contaminated laying on the patient's bed or may actually be knocked to the floor, such as in an emergency operation. Similarly, the rapid insertion and removal of syringes are problematic, because the syringes may be accidentally stuck into the patient, doctor, or nurse, which is especially dangerous, as it dramatically increases the transmission of certain diseases or viruses, such as the AIDS virus or Hepatitis C. In fact, with nearly six million healthcare professionals currently in practice, more than one million percutaneous injuries are reported annually in the healthcare setting, which translates to approximately one in six professional annually. "New Glove to Help Protect Healthcare Workers from Deadly Diseases," *Dallas-Ft. Worth Heathcare Journal* (November 1999; Volume 4, Number 2). Fearing such injuries, some health care professionals routinely miss work, postpone childbearing, and/or otherwise alter their personal lifestyles. In addition, if stuck with a needle, these health care professionals may be forced to take powerful drugs that cause severe side effects Likewise, speed is important, because the timing and transmission of many of these medicines is important to avoid calamities, such as aspiration pneumonia (e.g., when the patient vomits in his mask). Also, with the concern over the organization and coordination of the multiple syringes, the doctor's attention may be distracted from the patient and the administration of medications at a critical time. Finally, since multiple syringes are generally needed to induce unconsciousness, the anesthesiologist's hands are unnecessarily used to hold a syringe, which makes the anesthesiologist less efficient.

SUMMARY

An infusion apparatus comprises a plurality of ports (e.g., three syringe ports), a plurality of one-way directional valves (e.g., three), and, in certain embodiments, a joint. Each port is adapted to receive and secure a syringe to allow for the flow of liquid medication through the syringe into the port. Each one-way directional or unidirectional valve is in fluid communication with a respective port of the plurality of ports to enable the liquid to flow away from the port and into and through the respective one-way directional or unidirectional valve. Each port is typically in fluid communication with each one-way directional or unidirectional valve via intravenous tubing, but the one-way directional or unidirectional valve may be directly coupled to the port. If the joint is used, the joint has a plurality of inputs to receive the flow from the plurality of one-way directional valves or unidirectional valve. The inputs of the joint are in fluid communication with each individual port of the plurality of ports. The joint also has an output. Alternatively, the outputs from the ports can be coupled to multiple intravenous ports with unidirectional valves or the outputs of the unidirectional valves can be coupled to corresponding intravenous ports.

The ports are also preferably equipped to handle either needleless or needle bearing syringes. In addition, a locking apparatus secured to the joint may be used to secure the joint to an intravenous tubing port, which is, in turn, secured to intravenous tubing, and extends to the patient and actually enters the patient via a catheter inserted into the patient, e.g., the patient's arm.

Also, preferred embodiments are also comprised of a transparent cartridge to secure the plurality of ports, the unidirectional valves, and the joint together. The cartridge may be comprised of a plastic material. A syringe holder may also be used to hold and secure the syringes. The syringe holder may be attached to the cartridge or otherwise combined with the cartridge to form a single unit. Alternatively, the syringe holder may be used to hold and secure the syringes, which are, in turn, directly coupled with corresponding intravenous ports. A securing apparatus may also be used to secure the infusion apparatus in place. The infusion apparatus is preferably used to transfer liquid medicines from a syringe into a patient or via a continuous drip.

Preferred embodiments provide a number of advantages, important functions and key features. In particular, preferred embodiments enable the coordinated and simultaneous entry of certain drugs and medicines, such as drugs commonly used by anesthesiologists, namely (i) a hypnotic agent; (ii) muscle relaxant; and (iii) a narcotic. Preferred embodiments also secure the multiple syringes in a proper and stable position, so that the syringes do not become contaminated and do not harm the patient and/or other medical personnel. Preferred embodiments increase the speed of the administration of the medicines and allow for the dosages to be closely monitored and controlled. As stated above, this is especially important in applications concerning anesthesia medicines, as if the administration is not properly controlled, the patient can suffer aspiration pneumonia, in which the patient vomits in his mask. In these instances, the faster the medicines are administered, the better. Preferred embodiments increase the speed at which anesthesia medicines can be administered. Preferred embodiments are also equipped with a one way directional valve to prevent the contamination or back flow of medicine from one syringe into another syringe. And, in certain instances, although typically not with anesthesia drugs, drugs may interact with one another, and the preferred embodiment enables the drugs to be mixed together to some extent, prior to the entry into the patient. Also, preferred embodiments also use needless attachments and locks to secure the preferred embodiment to the syringe to the intravenous tubing in a safe manner. Finally, preferred embodiments are easily retrofitted into existing intravenous ports and intravenous tubing. Additional advantages will be evident after reviewing the description and drawings.

BRIEF DESCRIPTION OF THE DRAWINGS

The accompanying drawings are incorporated into and form a part of the specification to illustrate several examples of the present inventions. These drawings together with the description serve to explain the principles of the inventions. The drawings are only for the purpose of illustrating preferred and alternative examples of how the inventions can be made and used and are not to be construed as limiting the inventions to only the illustrated and described examples. Further features and advantages will become apparent from the following and more particular description of the various embodiments of the invention, as illustrated in the accompanying drawings, wherein.

DETAILED DESCRIPTION OF THE PREFERRED EMBODIMENT

Figure 1:
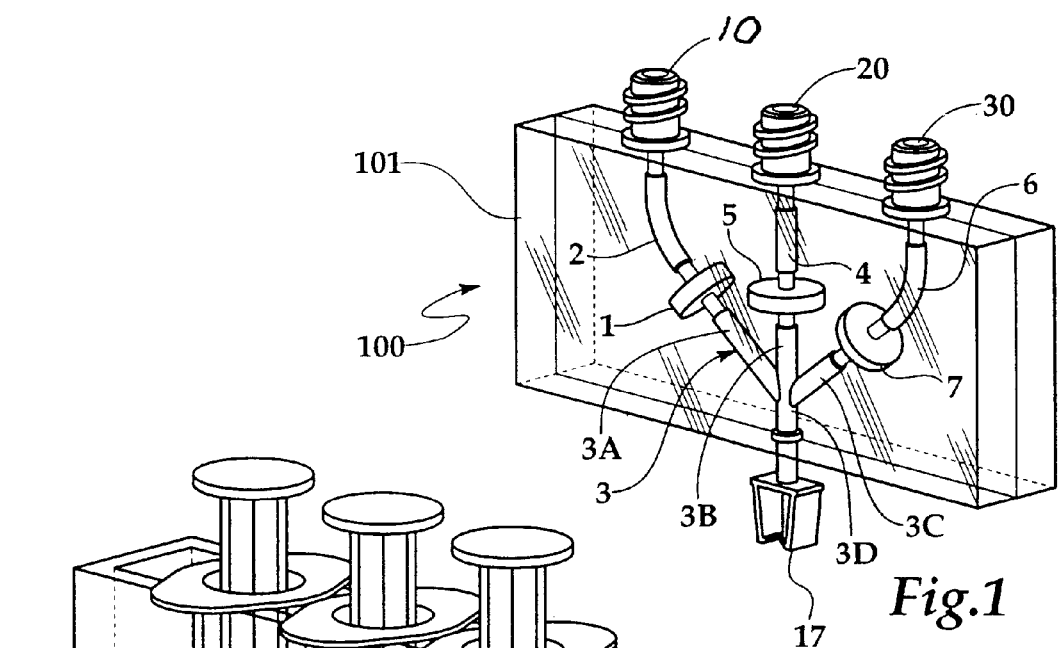
FIG. 1 is a perspective view a preferred embodiment of infusion device cartridge 100.

The preferred embodiment will be described by referring to apparatus showing various examples of how the inventions can be made and used. When possible, like reference characters are used throughout the several views of the drawing to indicate like or corresponding parts.

Figure 2:
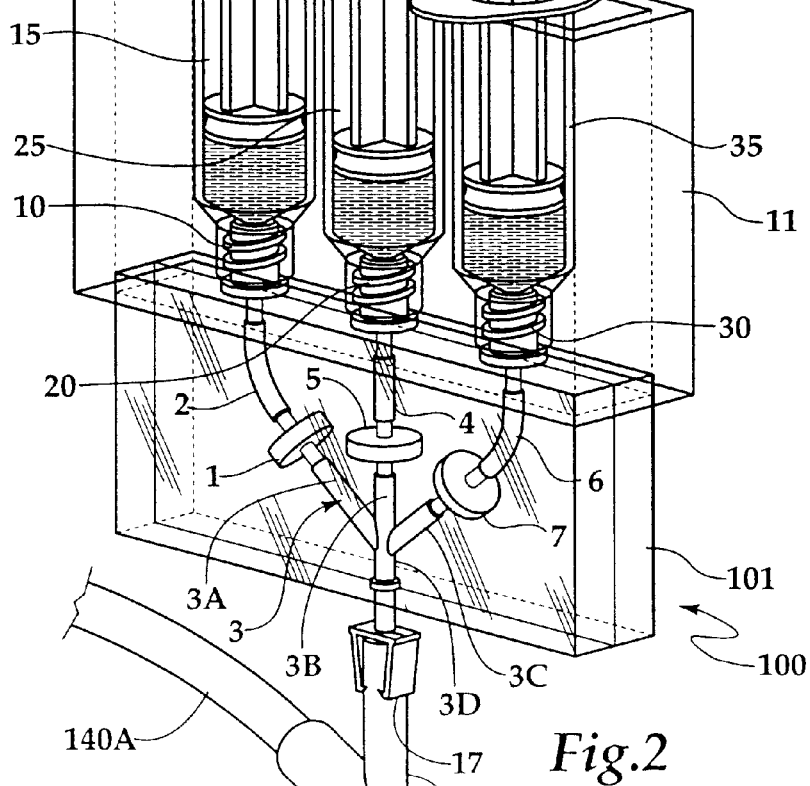
FIG. 2 is a perspective view of a preferred embodiment of infusion device cartridge 100 and holder 11; together with numerous syringes 15, 25, and 35; intravenous tubing 140A and 140B; and port 150.
Figures 6, 7:
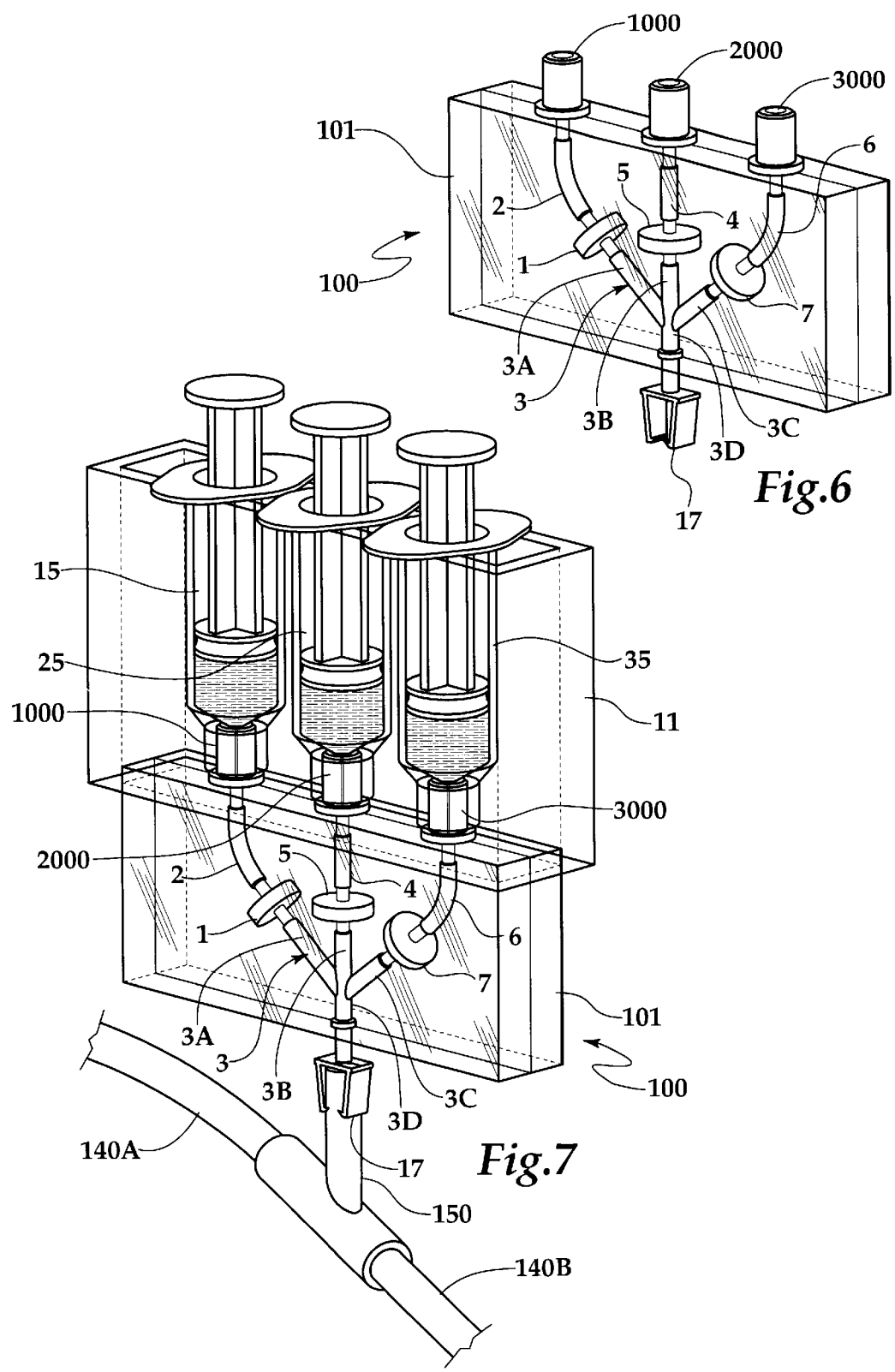
FIG. 6 is a perspective view an alternate preferred embodiment of infusion device cartridge 100, having ports 1000, 2000, and 3000 with a rubberized surface to receive syringes having needles.
FIG. 7 is a perspective view of an alternate preferred embodiment of infusion device cartridge 100, together with numerous syringes 15, 25, and 35, equipped with needles, and intravenous tubing 140A and 140B, port 150, and holder 11.

Referring to FIGS. 1 and 6, infusion device cartridge 100 has a plurality of injection ports 10, 20, and 30 (in FIG. 1) and injection ports 1000, 2000, and 3000 (in FIG. 6). While the injection ports 10, 20, and 30 incorporate needleless attachments for the use with needleless syringes 15, 25, and 35 (as shown in FIG. 2), which screw onto the needleless attachments affixed to injection ports 10, 20, and 30, alternate attachments or ports with a rubberized surface for syringes having a needle system may also be used, such as ports 1000, 2000, and 3000 in FIG. 6 for syringes 15, 25, and 35, when equipped with needles (as shown in FIG. 7). As shown in FIGS. 2 and 7, syringes 15, 25, and 35 are preferably secured in place by holder 11. Holder 11 has one or more cavities or openings designed to conform to individual, cylindrical bodies of syringes 15, 25, and 35, such that the bodies of syringes 15, 25, and 35 snap into position. Alternatively, cavities found in holder 11 may be partially open, so as to allow syringes 15, 25 and 35 to snap into position without having to be inserted into an opening or cavity. Holder 11, thus, removes the need to place syringes 15, 25, and 35 on a patient's bed or somewhere else in the hospital room as well as the need for a medical specialist, such as an anesthesiologist, to hold more than one syringe at a time (if any syringe needs to be held while administering medicine to the patient). The secure positioning of syringes 15, 25, and 35 also makes it easier to administer and control the administration (e.g., the timing and amount) of various medicines. Intravenous tubing 2, 4, and 6, respectively are attached to ports 10, 20, and 30. Intravenous tubing 2, 4, and 6 extend from ports 10, 20, and 30, respectively, to one-way or unidirectional valves 1, 5, and 7, respectively. Unidirectional valves 1, 5, and 7 are, in turn, inserted into openings 3A, 3B, and 3C of joint 3, which combines the inputs received from ports 10, 20, and 30 into a single port 3D. Single port 3D preferably includes a locking apparatus 17, such as a level lock cannula manufactured by B. D. Interlink, Becton Dickinson & Co., Franklin Lakes, N.J. 07417-1884, to secure infusion device cartridge 100 to intravenous tubing port 150, as shown in FIGS. 2 and 7. Unidirectional valves 1, 5, and 7 prevent the back flow of liquid medication from one syringe into another syringe or from infusion device cartridge 100 into a syringe, which prevents the contamination of one syringe by medication found in another syringe. The use of unidirectional valves 1, 5, and 7 prevent intravenous fluids from flowing back into the other medication syringes. Also, infusion device cartridge 100 also includes a plastic clear casing 101 to secure the various components, including ports 3A, 3B, and 3C; unidirectional valves 1, 5, and 7; joint 3; and various intravenous tubing 2, 4, and 6, together. The casing is clear to enable the anesthesiologist to view the flow and administration of the liquid medications from syringes 15, 25, and 35. Holder 11 is preferably also clear, so as to enable the contents of syringes 15, 25, and 35 to be easily viewed.

Figure 3A:
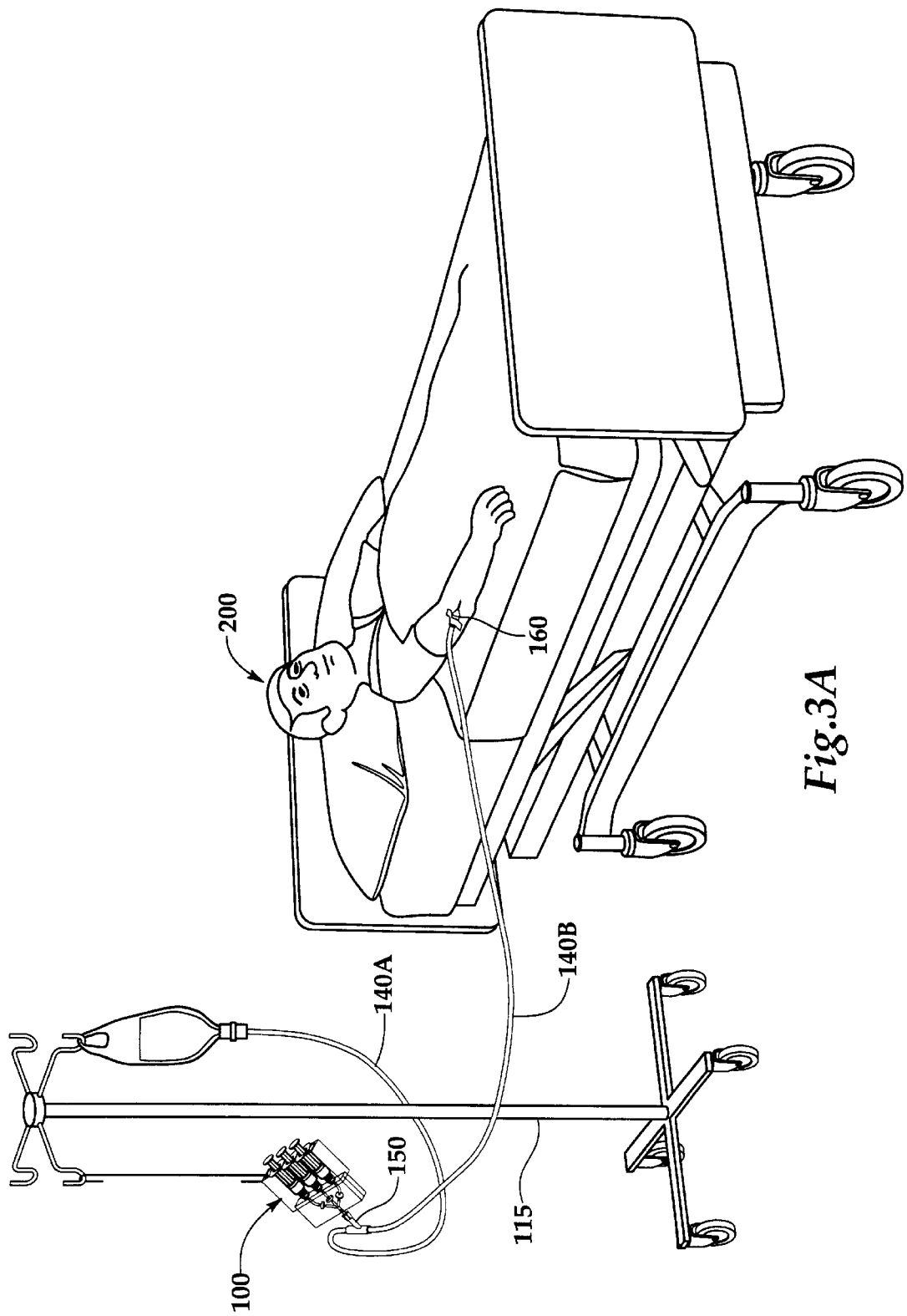
FIGS. 3A, 3B and 3C are perspective views of a preferred embodiment of infusion device cartridge 100 secured in various ways, together with intravenous tubing 140A and 140B and intravenous catheter 160 inserted into patient 200.
Figure 3B:
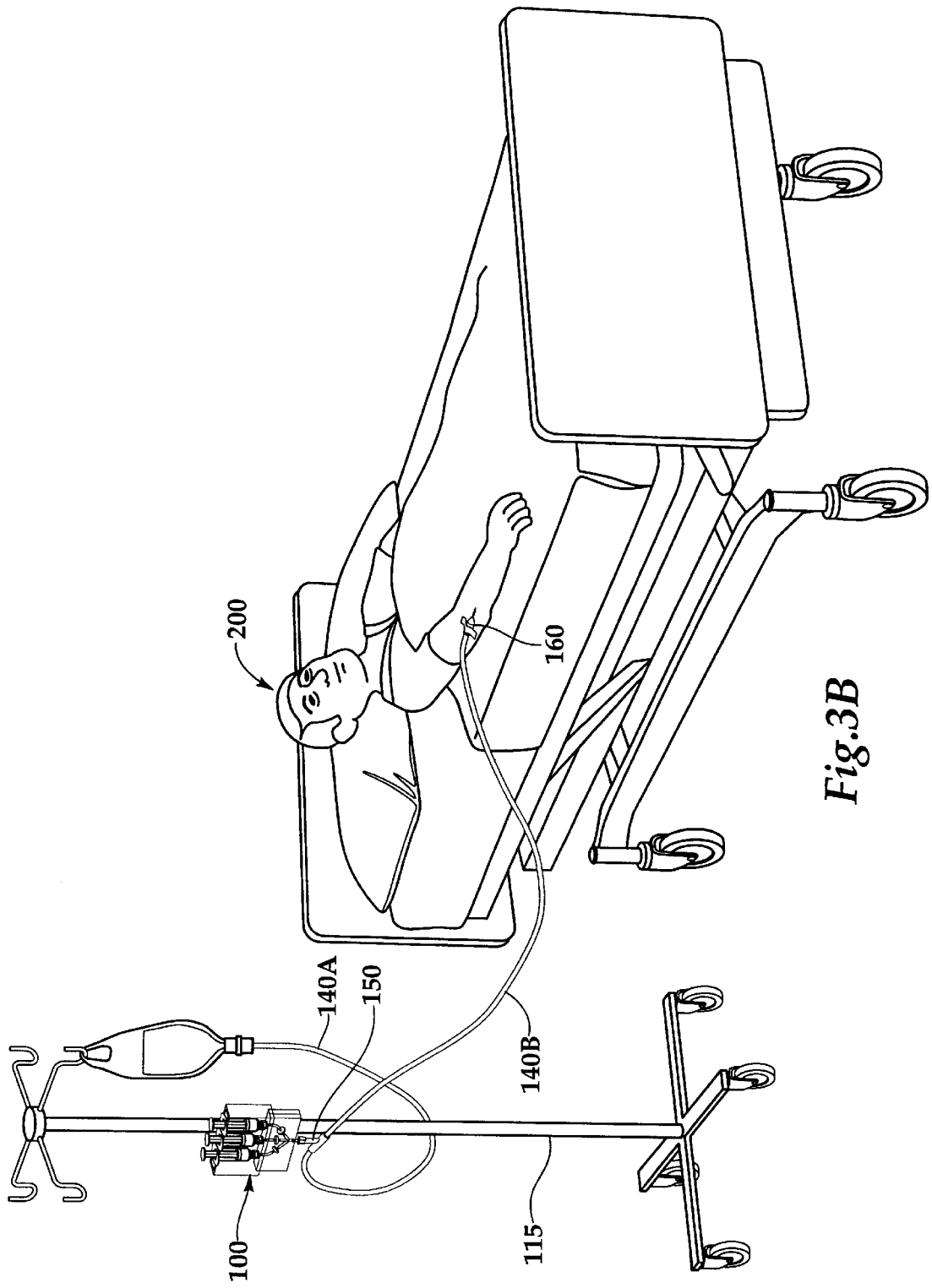
Figure 3C:
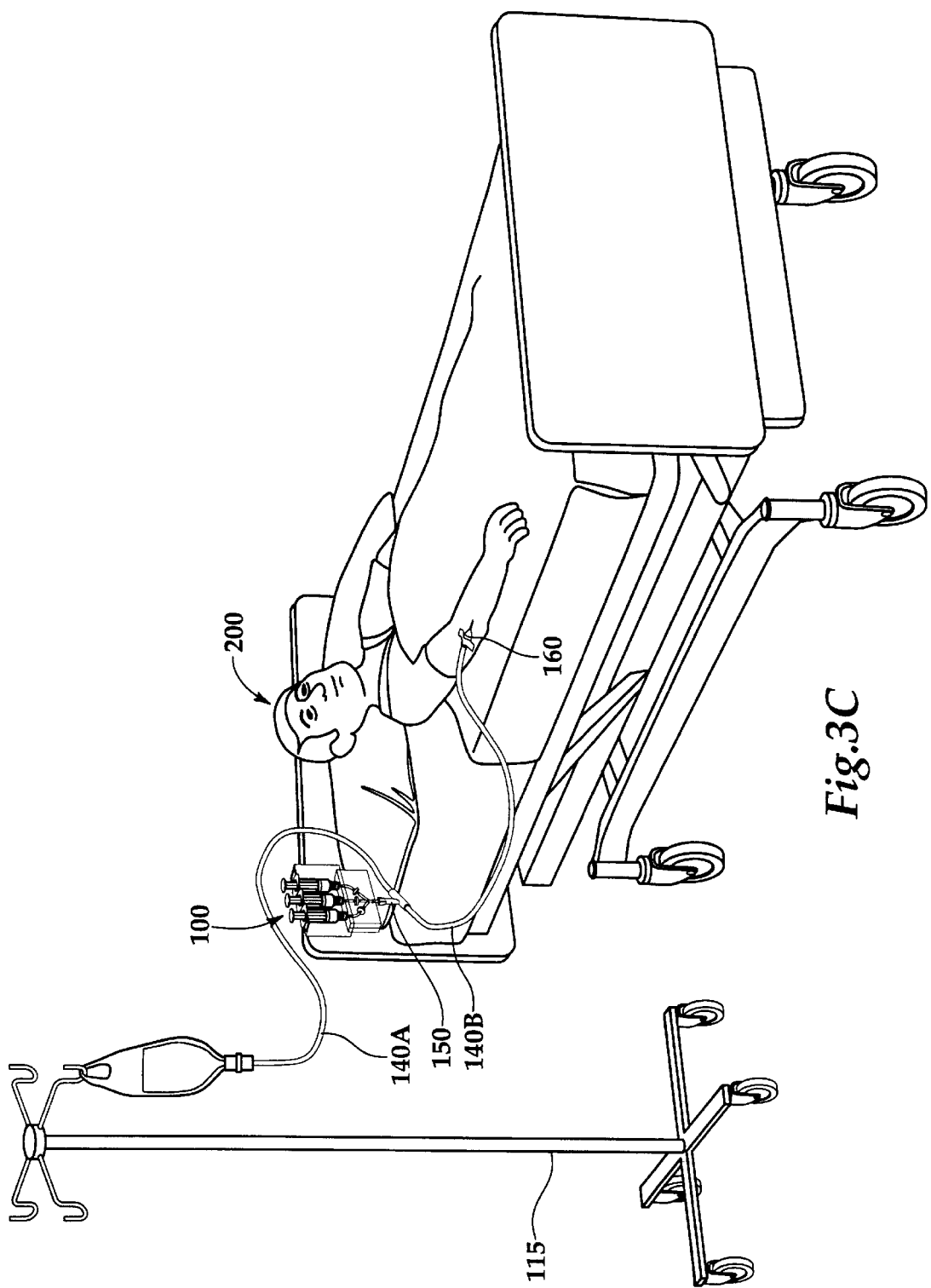

Referring to FIGS. 3A, 3B, and 3C, infusion device cartridge 100 can hang from intravenous pole 115, as shown in FIG. 3A; be clamped to intravenous pole 115, as shown in FIG. 3B; or secured to the patient's bed, as shown in FIG. 3C to support or secure infusion device cartridge 100. Alternatively, infusion device cartridge 100 can include a velcro material to secure infusion device cartridge 100 to another stable surface. Infusion device cartridge 100 is attached to intravenous tubing port 150, which is, in turn, connected via intravenous tubing 140B to intravenous catheter 160 that is inserted into the arm of patient 200.

Figure 4:
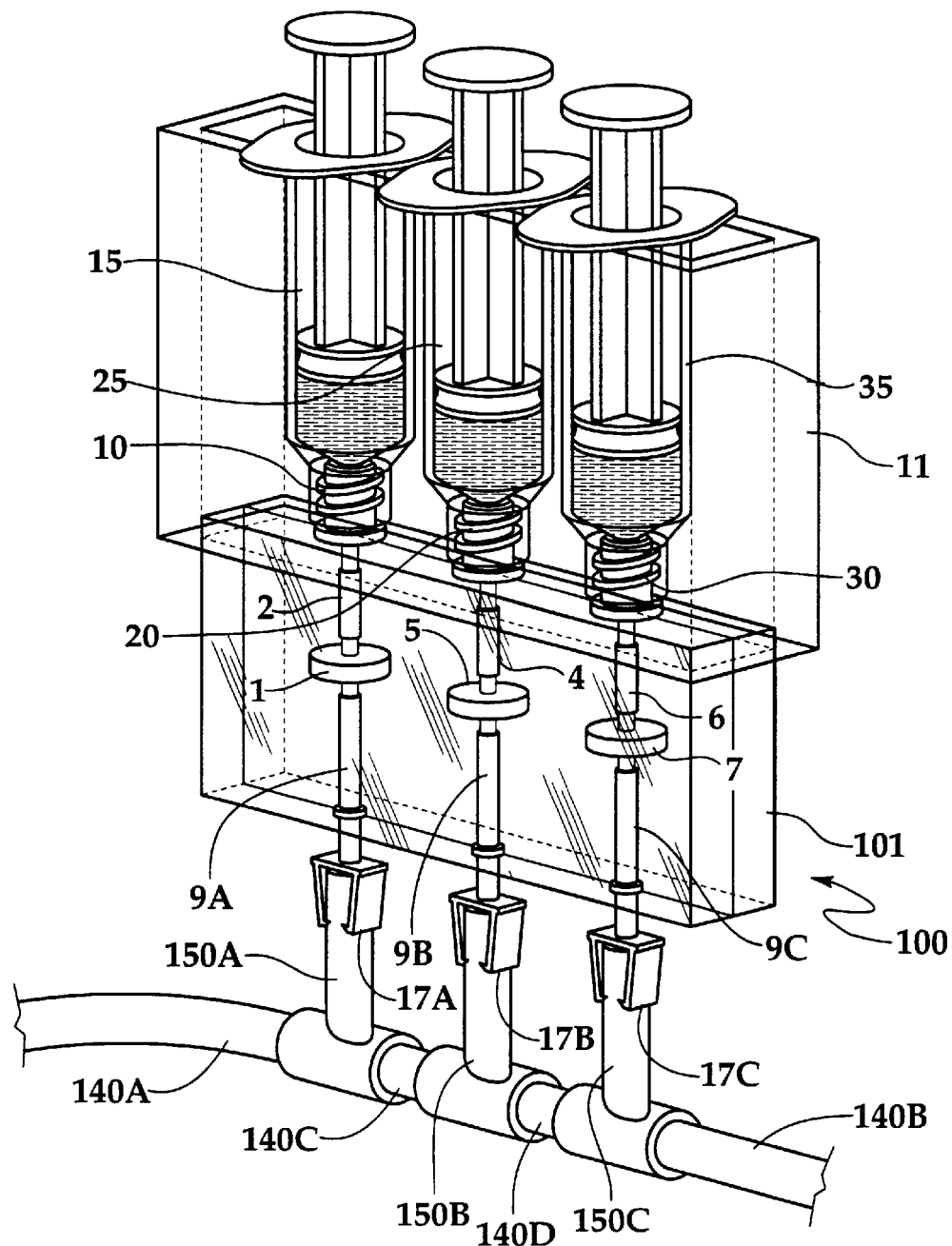
FIG. 4 is a perspective view of an alternate preferred embodiment of infusion device cartridge 100 and holder 11, together with numerous syringes 15, 25, and 35; one-way valves 1, 5, and 7; intravenous tubing 140A, 140B, 140C, and 140D; and ports 150A, 150B, and 150C.

FIG. 4 shows infusion device cartridge 100 with a plurality of injection ports 10, 20, and 30. Once again, while the injection ports 10, 20, and 30 incorporate needleless attachments for the use with needleless syringes 15, 25, and 35, which screw onto the needleless attachments affixed to injection ports 10, 20, and 30, alternate attachments or ports with a rubberized surface for syringes having needles may also be used. Similarly, syringes 15, 25, and 35 are preferably secured in place by holder 11. Holder 11 has one or more cavities or openings designed to conform to individual, cylindrical bodies of syringes 15, 25, and 35, such that the bodies of syringes 15, 25, and 35 snap into position. Alternatively, cavities found in holder 1 may be partially open, so as to allow syringes 15, 25 and 35 to snap into position without having to be inserted into an opening or cavity. Holder 11, thus, removes the need to place syringes 15, 25, and 35 on a patient's bed or somewhere else in the hospital room as well as the need for a medical specialist, such as an anesthesiologist, to hold more than one syringe at a time (if any syringe needs to be held while administering medicine to the patient). The secure positioning of syringes 15, 25, and 35 also makes it easier to administer and control the administration (e.g., the timing and amount) of various medicines. Intravenous tubing 2, 4, and 6, respectively, are attached to ports 10, 20, and 30. Intravenous tubing 2, 4, and 6 extend from ports 10, 20, and 30, respectively, to one-way or unidirectional valves 1, 5, and 7, respectively. Unidirectional valves 1, 5, and 7 are, in turn, inserted into or coupled with intravenous tubing 9A, 9B, or 9C, which, in turn, are connected to locking apparatus 17A, 17B, and 17C to secure infusion device cartridge 100 to intravenous tubing ports 150A, 150B, and 150C. Ports 150A and 150B are joined by intravenous tubing 140C; ports 150B and 150C are jointed by intravenous tubing 140D. Once again, unidirectional valves 1, 5, and 7 prevent the back flow of liquid medication from one syringe into another syringe, which prevents the contamination of one syringe by medication found in another syringe. The use of unidirectional valves 1, 5, and 7 prevent intravenous fluids from flowing back into the other medication syringes. Further, as before, infusion device cartridge 100 also includes a plastic clear casing 101 to secure the various components, including unidirectional valves 1, 5, and 7; and various intravenous tubing 2, 4, 6, 9A, 9B, and 9C, together, and the casing and holder are clear to enable the anesthesiologist to view the syringes and the flow and administration of the liquid medications from syringes 15, 25, and 35. The alternate embodiment shown in FIG. 4 can be used in a fashion similar to the embodiment shown in FIGS. 3A, 3B, and 3C.

Figure 5:
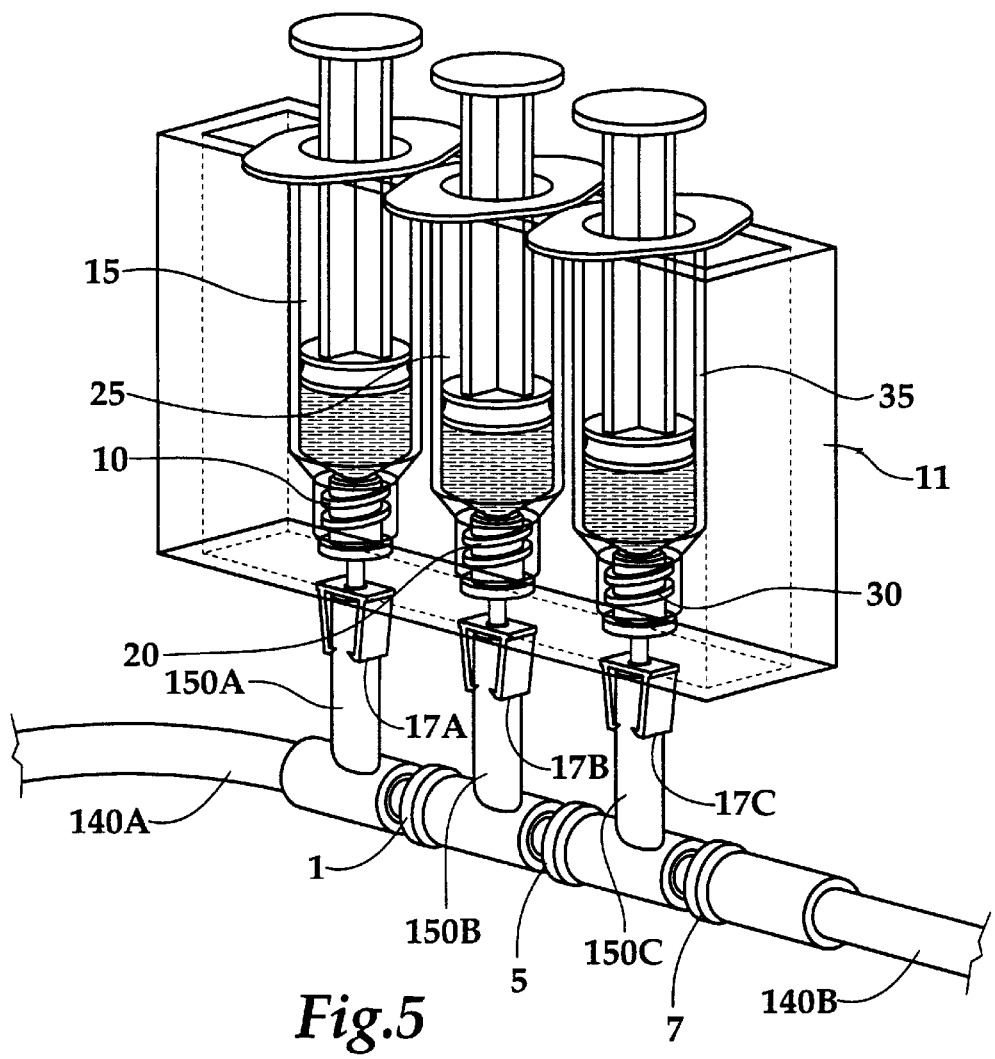
FIG. 5 is a perspective view of an alternate preferred embodiment showing holder 11; together with numerous syringes 15, 25, and 35; one way valves 1, 5, and 7; intravenous tubing 140A and 140B; and ports 150A, 150B, and 150C.

FIG. 5 shows holder 11 with a plurality of injection ports 10, 20, and 30. Once again, while the injection ports 10, 20, and 30 incorporate needleless attachments for the use with needleless syringes 15, 25, and 35, which screw onto the needleless attachments affixed to injection ports 10, 20, and 30, alternate attachments or ports with a rubberized surface for syringes having needles may also be used. As before, holder 11 has one or more cavities or openings designed to conform to individual, cylindrical bodies of syringes 15, 25, and 35, such that the bodies of syringes 15, 25, and 35 snap into position. Alternatively, cavities found in holder 11 may be partially open, so as to allow syringes 15, 25 and 35 to snap into position without having to be inserted into an opening or cavity. Holder 11, thus, removes the need to place syringes 15, 25, and 35 on a patient's bed or somewhere else in the hospital room as well as the need for a medical specialist, such as an anesthesiologist, to hold more than one syringe at a time (if any syringe needs to be held while administering medicine to the patient). The secure positioning of syringes 15,25, and 35 also makes it easier to administer and control the administration (e.g., the timing and amount) of various medicines. In this embodiment, the outputs from syringes 15, 25, and 35 are directly channeled into ports 150A, 150B, and 150C, respectively and ports 10, 20, and 30 are secured to ports 150A, 150B, and 150C with locking apparatus 17A, 17B, and 17C. In this embodiment, unidirectional valves 1, 5, and 7 are positioned between ports 150A and 150B; between ports 150B and 150C; and port 150C and the patient. In fact, ports 150A and 150B are preferably joined with unidirectional valve 1; ports 150B and 150C are joined with unidirectional valve 5. As explained above, unidirectional valves 1, 5, and 7 prevent the back flow of liquid medication from one syringe into another syringe, which prevents the contamination of one syringe by medication found in another syringe. The use of unidirectional valves 1, 5, and 7 prevent intravenous fluids from flowing back into the other medication syringes. And, as before, holder 11 is clear to enable the anesthesiologist to view the syringes and the flow and administration of the liquid medications from syringes 15,25, and 35. The alternate embodiment shown in FIG. 5 can be used in a fashion similar to the embodiment shown in FIGS. 3A, 3B, and 3C.

FURTHER MODIFICATIONS AND VARIATIONS

Although the invention has been described with reference to a specific embodiment, this description is not meant to be construed in a limiting sense. The example embodiments shown and described above are only intended as an example. Various modifications of the disclosed embodiment as well as alternate embodiments of the invention will become apparent to persons skilled in the art upon reference to the description of the invention. For instance, alternate types of ports as well as various numbers of ports can be used as well as alternate mechanisms to secure the syringes to the infusion device cartridge or the infusion device cartridge to another device.

Thus, even though numerous characteristics and advantages of the present inventions have been set forth in the foregoing description, together with details of the structure and function of the inventions, the disclosure is illustrative only, and changes may be made in the detail, especially in matters of shape, size and arrangement of the parts within the principles of the inventions to the full extent indicated by the broad general meaning of the terms used in the attached claims. Accordingly, it should be understood that the modifications and variations suggested above and below are not intended to the exhaustive. These examples help show the scope of the inventive concepts, which are covered in the appended claims. The appended claims are intended to cover these modifications and alternate embodiments.

In short, the description and drawings of the specific examples above are not intended to point out what an infringement of this patent would be, but are to provide at least one explanation of how to make and use the inventions contained herein. The limits of the inventions and the bounds of the patent protection are measured by and defined in the following claims.

What is claimed is:

1. An infusion apparatus, comprising:
   (a) a plurality of ports, each port adapted to receive and secure a corresponding syringe to allow for a flow of a liquid from said corresponding syringe into and through said port of said plurality of ports, wherein each port of said plurality of ports enables said corresponding syringe to be removed and replaced with another syringe at will;
   (b) a plurality of one-way directional valves, each one-way directional valve in fluid communication with a respective port of said plurality of ports to enable said liquid to flow from said port of said plurality of ports and away from said port of said plurality of ports to created a liquid flow;
   (c) a joint having a plurality of inputs to receive said liquid flow from said plurality of one-way directional valves, each input of said plurality of inputs in fluid communication with a corresponding individual port of said plurality of ports via a one-way directional valve, said joint having an output to direct said liquid flow received from plurality of one-way directional valves away from said joint, said joint also having a y-shaped structure positioned after said plurality of inputs and before said output; and
   (d) a cartridge embracing said joint and said plurality of one-way directional valves, said cartridge to secure said plurality of ports, said plurality of one-way directional valves, and said joint together into a single unit, said cartridge to secure said plurality of ports in a fixed position to enable said syringe to be easily received, removed, and replaced at will.

2. The infusion apparatus of claim 1, wherein each port of said plurality of ports are needleless ports.

3. The infusion apparatus of claim 1, wherein said syringe is equipped with a needle and each port of said plurality of ports is equipped to receive said needle.

4. The infusion apparatus of claim 1, further comprising a locking apparatus secured to said joint to secure said output of said joint to an intravenous tubing port.

5. The infusion apparatus of claim 4, wherein said intravenous tubing port is secured to intravenous tubing.

6. The infusion apparatus of claim 5, wherein said intravenous tubing extends to a patient.

7. The infusion apparatus of claim 1, wherein said cartridge is comprised of plastic material.

8. The infusion apparatus of claim 1, wherein said cartridge is transparent to enable said flow of said liquid to be monitored.

9. The infusion apparatus of claim 1, wherein said liquid is a medicine.

10. The infusion apparatus of claim 9, wherein said medicine is anesthesia medicine.

11. The infusion apparatus of claim 10, wherein said anesthesia medicine is selected from a group consisting of a hypnotic agent, a muscle relaxant, and a narcotic.

12. The infusion apparatus of claim 1, further comprising a syringe holder to hold and secure each said syringe secured to each port of said plurality of ports.

13. The infusion apparatus of claim 12, wherein said syringe holder used to hold and secure each said corresponding syringe received by and secured to each port of said plurality of ports is further comprised of a hollow housing enclosing said plurality of ports and a portion of each corresponding syringe sufficient to secure each said corresponding syringe to each port of said plurality of ports, said hollow housing having a first opening to permit each port of said plurality of ports to be inserted inside said hollow housing and a second opening to permit each said corresponding syringe to extend outside said hollow housing to be operated and to be removed at will from each port of said plurality of ports.

14. The infusion apparatus of claim 1, wherein each port is in fluid communication with each one-ay directional valve via intravenous tubing.

15. The infusion apparatus of claim 1, further comprising a securing apparatus to secure said infusion apparatus in a fixed location.

16. The infusion apparatus of claim 1, further wherein said output of said joint extends out of said cartridge.

17. The infusion apparatus of claim 1, further wherein said cartridge surrounds said joint and said plurality of one-way directional valves.

18. An infusion apparatus, comprising:
   (a) a first syringe port adapted to receive and secure a first syringe to allow for a first flow of a first liquid from said first syringe into said first syringe port;
   (b) a second syringe port adapted to receive and secure a second syringe to allow for a second flow of a second liquid from said second syringe into said second syringe port;
   (c) a first unidirectional valve in fluid communication with said first syringe port to receive and enable said first flow of said first liquid from said first syringe to continue and to prevent any backflow of any liquid into said fist syringe;
   (d) a second unidirectional valve in fluid communication with said second syringe port to receive and enable said second flow of said second liquid from said second syringe to continue and to prevent any backflow of any liquid into said second syringe;
   (e) a joint having a first input port and a second input port, said first input port in fluid communication with said first unidirectional valve to receive said first flow and said second input port in fluid communication with said second unidirectonal valve to receive said second flow, said joint having a y-shaped structure positioned between said first input port and said second input port together and said output port, said joint connecting said first input port and said second input port to an output port to enable said first flow of said first liquid received from said first input port and said second flow of said second liquid received from said second input port to continue out of said output; and
   (f) a cartridge to secure said first syringe port and said second syringe port, said first unidirectional valve and said second unidirectional valve, and said joint together, said cartridge to embrace said first unidirectional valve and said second unidirectional valve and said joint, said cartridge to secure said first syringe port and said second syringe port into a fixed position to enable said first syringe and said syringe to be easily received, removed, and, if necessary, replaced.

19. The infusion apparatus of claim 18, further comprising:
   (g) a third syringe port adapted to receive and secure a third syringe to allow for a third flow of a third liquid from said third syringe into said third syringe port;
   (h) a third unidirectional valve in fluid communication with said third syringe port to receive and enable said third flow of said third liquid from said third syringe to continue and to prevent any backflow of any liquid into said third syringe; and wherein said joint having a third input port in fluid communication with said third unidirectional valve to receive said third flow of said third liquid and said joint connecting said third input port to said output; and further wherein said joint having a y-shaped structure positioned between said first input port, said second input port, and third input port together and said output port, said joint having a y-shaped structure positioned between said first input port, said second input port, and said third input port together and said output port, said joint connecting said first input port, said second input port, and said third input port to an output port to enable said first flow of said first liquid received from said first input port and said second flow of said second liquid received from said second input port and said third flow of said third liquid to continue out of said output; and further wherein said joint cartridge to secure said first syringe port and said second syringe port, said third syringe port, said first unidirectional valve, said second unidirectional valve, said third unidirectional valve, and said joint together, said cartridge to embrace said first unidirectional valve, said second unidirectional valve, said third unidirectional valve, and said joint together, said cartridge to secure said third syringe port into a fixed position to enable said third syringe to be easily received, removed, and, if necessary, replaced.

20. The infusion apparatus of claim 18, wherein said first syringe port and said second syringe port are needleless.

21. The infusion apparatus of claim 18, further comprising a locking apparatus secured to said output of said joint to secure said output to an intravenous tubing port.

22. The infusion apparatus of claim 18, wherein said cartridge is transparent to enable said first the flow of said first liquid and said second flow of said second liquid to be monitored.

23. The infusion apparatus of claim 18, wherein said first liquid and said second liquid are anesthesia medicines selected from a group consisting of a hypnotic agent, a muscle relaxant, and a narcotic.

24. The infusion apparatus of claim 18, further comprising a syringe holder to hold and secure said first syringe and said second syringe.

25. The infusion apparatus of claim 18, wherein said syringe holder used to hold said first syringe and said second syringe is further comprised of a hollow housing enclosing said first syringe port and said second syringe port and a portion of said syringe and said second syringe sufficient to secure said first syringe to said first syringe port and said second syringe to said second syringe port, said hollow housing having a first opening to permit said first syringe port and said second syringe port to be inserted inside said hollow housing and a second opening to permit said first syringe and said second syringe to extend outside said hollow housing to permit said first syringe and said second syringe be operated and to be removed at will from said first syringe port and said second syringe port, respectively.

26. The infusion apparatus of claim 18, further wherein said output of said joint extends out of said cartridge.

27. The infusion apparatus of claim 18, further wherein said cartridge encloses said first unidirectional valve and said second unidirectional valve and said joint.

* * * * *